United States Patent
Wang et al.

(10) Patent No.: US 10,898,425 B2
(45) Date of Patent: Jan. 26, 2021

(54) SKIN ENGAGING MEMBER COMPRISING ETHYLENE VINYL ACETATE AND A FRAGRANCE

(71) Applicant: The Gillette Company LLC, Boston, MA (US)

(72) Inventors: Xiandong Wang, Acton, MA (US); Valerie Jean Bradford, Framingham, MA (US); Keesha Alicia Hayes, Cambridge, MA (US); Michael John Moloney, Brimfield, MA (US); Peter Michael Ries, Cambridge, MA (US); Joia Kirin Spooner-Fleming, Jamaica Plain, MA (US); Virginia Tzung-Hwei Hutchins, Cincinnati, OH (US); Zerlina Guzdar Dubois, Mason, OH (US)

(73) Assignee: The Gillette Company LLC, Boston, MA (US)

( * ) Notice: Subject to any disclaimer, the term of this patent is extended or adjusted under 35 U.S.C. 154(b) by 0 days.

(21) Appl. No.: 15/815,896

(22) Filed: Nov. 17, 2017

(65) Prior Publication Data

US 2018/0133139 A1    May 17, 2018

Related U.S. Application Data

(60) Provisional application No. 62/423,508, filed on Nov. 17, 2016.

(51) Int. Cl.
| A61K 8/81 | (2006.01) |
| A61K 8/86 | (2006.01) |
| A61Q 9/02 | (2006.01) |
| B26B 21/44 | (2006.01) |

(52) U.S. Cl.
CPC .............. *A61K 8/8135* (2013.01); *A61K 8/86* (2013.01); *A61Q 9/02* (2013.01); *B26B 21/443* (2013.01); *A61K 2800/56* (2013.01); *A61K 2800/594* (2013.01); *A61K 2800/87* (2013.01)

(58) Field of Classification Search
CPC ................................. A61Q 9/02; B26B 21/443
See application file for complete search history.

(56) References Cited

U.S. PATENT DOCUMENTS

| 3,111,127 A | 11/1963 | Jarboe |
| 3,917,613 A | 11/1975 | Humbert et al. |
| 3,991,178 A | 11/1976 | Humbert et al. |
| 4,029,759 A | 6/1977 | Humbert et al. |
| 4,136,163 A | 1/1979 | Watson et al. |
| 4,150,052 A | 4/1979 | Watson et al. |
| 4,153,679 A | 5/1979 | Rowsell et al. |
| 4,157,384 A | 6/1979 | Browning et al. |
| 4,178,459 A | 12/1979 | Rowsell et al. |
| 4,230,688 A | 10/1980 | Rowsell et al. |
| 4,459,425 A | 7/1984 | Amano |
| 5,095,619 A | 3/1992 | Davis et al. |
| 5,134,775 A | 8/1992 | Althaus et al. |
| 5,266,592 A | 11/1993 | Grub et al. |
| 5,349,750 A * | 9/1994 | Tseng .................... A61K 8/8135 30/32 |
| 5,451,404 A | 9/1995 | Furman |
| 5,454,164 A | 10/1995 | Yin et al. |
| 5,483,466 A | 1/1996 | Kawahara et al. |
| 5,551,152 A | 9/1996 | Tseng |
| 5,608,119 A | 3/1997 | Amano et al. |
| 5,653,971 A | 8/1997 | Badin et al. |
| 5,665,339 A | 9/1997 | Simmons |
| 5,703,123 A | 12/1997 | Pelzer et al. |
| 5,711,076 A | 1/1998 | Yin et al. |
| 5,713,131 A | 2/1998 | Rogers et al. |
| 5,725,865 A | 3/1998 | Mane et al. |
| 5,956,848 A | 9/1999 | Tseng et al. |
| 5,977,166 A | 11/1999 | Greenberg |
| 6,161,288 A | 12/2000 | Andrews |
| 6,295,733 B1 | 10/2001 | Wexler et al. |
| 6,298,558 B1 | 10/2001 | Tseng et al. |
| 6,298,559 B1 | 10/2001 | Kwiecien et al. |
| 6,301,785 B1 | 10/2001 | Kwiecien et al. |
| 6,302,785 B1 | 10/2001 | McKinney et al. |
| 6,365,215 B1 | 4/2002 | Grainger et al. |
| 6,442,839 B1 | 9/2002 | Tseng et al. |
| 6,449,849 B1 | 9/2002 | Hackerman |
| 6,451,811 B2 | 9/2002 | Vaillancourt et al. |
| 6,592,884 B2 | 7/2003 | Hofmann et al. |
| 6,884,903 B2 | 4/2005 | Lorenz et al. |
| 6,897,195 B2 | 5/2005 | Su et al. |
| 6,944,952 B1 | 9/2005 | Tseng |

(Continued)

FOREIGN PATENT DOCUMENTS

| AU | 2017362347 A1 | 4/2019 |
| BR | 112019009754 A2 | 5/2018 |

(Continued)

OTHER PUBLICATIONS

Watson, H.R., et al.; "New compounds with the menthol cooling effect"; J. Soc. Cosmet. Chem. (1978), 29, 185-200.
Koopmans, R.J., et al.; "Quantitative Measurements of the Vinylacetate Content in High Pressure Ethylene Vinylacetate Copolymers"; J. Adhesion, 1983, vol. 15, pp. 117-123.
Wei, E.T., et al.; "AG-3-5: a chemical producing sensations of cold"; J. Pharm. Pharmacol. (1983), 35(2):110-112.
Williams, K.R.; "Analysis of Ethylene-Vinyl Acetate Copolymers: A Combined TGA/FTIR Experiment"; J. Chem. Educ., 1994, 71(8), p. A195-A198.
Eccles, R.; "Menthol and related compounds"; J. Pharm. Pharmacol., (1994), 46, 618-630.
International Search Report and Written Opinion of the International Searching Authority; European Patent Application No. PCT/US2017/062124; dated Mar. 8, 2018; European Patent Office; Rijswijk, Netherlands.

(Continued)

*Primary Examiner* — Monica A Shin
(74) *Attorney, Agent, or Firm* — Kevin C. Johnson

(57) ABSTRACT

A skin engaging member suitable for use in a hair removal device, said skin engaging member comprising ethyl vinyl acetate having a low level of vinyl acetate, a water soluble polymer, and a fragrance composition.

10 Claims, 2 Drawing Sheets

(56) References Cited

U.S. PATENT DOCUMENTS

| | | | |
|---|---|---|---|
| 6,956,139 | B2 | 10/2005 | Green et al. |
| 7,024,776 | B2 | 4/2006 | Wain |
| 7,115,282 | B2 | 10/2006 | Shefer et al. |
| 7,121,754 | B2 | 10/2006 | Bressler et al. |
| 7,168,173 | B2 | 1/2007 | Worrick, III |
| 7,189,760 | B2 | 3/2007 | Erman et al. |
| 7,197,825 | B2 | 4/2007 | Walker et al. |
| 7,482,373 | B2 | 1/2009 | Wang et al. |
| 7,581,318 | B2 | 9/2009 | Coffin |
| 7,607,230 | B2 | 10/2009 | Aviza et al. |
| 2003/0082219 | A1 | 5/2003 | Warren et al. |
| 2004/0181943 | A1 | 9/2004 | Kwiecien |
| 2005/0019356 | A1 | 1/2005 | Bissett et al. |
| 2006/0225285 | A1 | 10/2006 | Slavtcheff et al. |
| 2006/0272155 | A1 | 12/2006 | Mehta et al. |
| 2008/0034590 | A1 | 2/2008 | Prudden et al. |
| 2008/0060201 | A1 | 3/2008 | Kwiecien |
| 2008/0069784 | A1 | 3/2008 | Millikin et al. |
| 2008/0241201 | A1* | 10/2008 | Warr ................. A61K 8/33 424/401 |
| 2008/0300314 | A1 | 12/2008 | Galopin et al. |
| 2009/0049695 | A1 | 2/2009 | Keene et al. |
| 2009/0223057 | A1 | 9/2009 | Coope-Epstein et al. |
| 2013/0230476 | A1* | 9/2013 | Pelzer ................. C11B 9/008 424/70.1 |
| 2015/0272847 | A1* | 10/2015 | Wang ................. A61K 8/35 30/41 |
| 2018/0133139 | A1 | 5/2018 | Wang et al. |

FOREIGN PATENT DOCUMENTS

| | | |
|---|---|---|
| CN | 109843385 A | 6/2019 |
| EP | 310299 A1 | 4/1989 |
| EP | 3541476 A1 | 9/2019 |
| GB | 1315626 A | 5/1973 |
| WO | 9205929 A1 | 4/1992 |
| WO | WO-9601172 A1 * 1/1996 ......... B26B 21/4087 |
| WO | 2005049553 A1 | 6/2005 |
| WO | 2006103401 A2 | 10/2006 |
| WO | 2007115593 A1 | 10/2007 |
| WO | 2011047221 A1 | 4/2011 |
| WO | 2015148308 A1 | 10/2015 |
| WO | 2016085729 A1 | 6/2016 |
| WO | 2017200990 A1 | 11/2017 |
| WO | 2018094124 A1 | 5/2018 |

OTHER PUBLICATIONS

International Preliminary Report on Patentability and Written Opinion of the International Searching Authority; European Patent Application No. PCT/US2017/062124; dated May 21, 2019; European Patent Office; Munich, Germany.

Fyfe, Padraig; Examination Report No. 1; Australian Patent Application No. 2017362347; dated Sep. 18, 2019; Australian Patent Office; Australia.

Schick Uses Scent to Give Men's Razor a Competitive Edge By Andrew Adam NewmanJun. 12, 2011 https://www.nytimes.com/2011/06/13/business/media/13adco.html.

* cited by examiner

SKIN ENGAGING MEMBER COMPRISING ETHYLENE VINYL ACETATE AND A FRAGRANCE

BACKGROUND OF THE INVENTION

Many razor cartridges include skin engaging members, commonly referred to as lubrication strips. These lubrication strips are typically present behind the blades in an aft position such that as a user performs a shave stroke, the skin is contact by the blades prior to contact by the skin engaging member. Many different types of skin engaging members have been disclosed. See e.g., U.S. Pat. Nos. 7,121,754; 6,298,558; 5,711,076; 5,134,775; 6,301,785; U.S. Patent Publ. Nos. 2009/0223057, 2004/181943, 2006/0225285, and 2006/0272155, 2008/060201A1; and WO 2011/047211. Some skin engaging members contain one or more types of polyethylene oxide (PEO) with water insoluble polymers such as polystyrene.

One problem with the use of polystyrene is that it requires high processing temperatures during extrusion. The high processing temperatures can adversely impact the integrity of chemicals in the skin engaging members potentially degrading them which can possibly impact consumer experience during use or product life cycle. The processing conditions required when using polystyrene can also limit what ingredients can be incorporated into the skin engaging member as certain materials cannot be subjected to such temperatures or processing conditions.

Use of ethylene vinyl acetate as a water insoluble polymer has also been suggested. See e.g. U.S. Pat. Nos. 5,349,750, 5,454,164, and 5,551,152. Though ethylene vinyl acetate has been generally described as a potential water insoluble polymer for use in a skin engaging member, many factors, including level of ingredients, grade of ethylene vinyl acetate, and processing conditions can impact the suitability of the skin engaging member for actual use. U.S. Pat. No. 5,551,152, for example mentions skin engaging member composites which can have 10-50% ethylene vinyl acetate and 50-90% of skin engaging member material, with commercial grades of vinyl acetate ranging in vinyl acetate content from 5-50% by weight. This reference goes on to provide several examples of skin engaging members with vinyl acetate having vinyl acetate content at 25% (Elvax 360).

Despite the earlier attempts, there remains a need for skin engaging members that provide the right amount of lubrication and consistent lubrication over multiple uses where the product retains a sufficient effective lifespan (which can include structural integrity and/or ability of the skin engaging member to continue providing a certain degree of lubrication after multiple uses). This is a significant challenge given shaving conditions vary by user based on individual shaving habit and environmental conditions; when designing products that are robust and can provide desirable lubrication yet retain structural integrity over multi-uses (in some instances up to 6 shaves, even as much as 12 shaves).

As such, there remains a need for a new skin engaging member which can be processed at a wider range of operating conditions, particularly when considering extrusion type methods but still provide desirable lubrication over the life of the product. These and other benefits may be addressed by one or more embodiments of the following invention. Further, there has long been a desire for skin engaging members which can provide added benefits beyond lubrication, one of these benefits can be the delivery of scent.

SUMMARY OF THE INVENTION

One aspect of this invention relates to a skin engaging member, suitable for use with a hair removal device, such as a razor or depilatory and scraping tool, said skin engaging member comprising a water soluble polymer and a non-water soluble polymer comprising ethylene vinyl acetate and a fragrance composition, such as fragrance RM as described hereinafter. This skin engaging member can be used on a hair removal device such as a razor.

The skin engaging member comprises ethylene vinyl acetate having a vinyl acetate % of about 18% or less. In one embodiment, the skin engaging member has a total vinyl acetate level of from about 0.2% up to 7.5%, by weight of the skin engaging member, preferably from about 0.4% to about 5.75%. In one embodiment the skin engaging member comprises about 50% to about 78% of a water-soluble polymer; about 20% to about 40% of ethylene vinyl acetate by weight of the skin engaging member, preferably from about 26% to about 32%, said ethylene vinyl acetate having a vinyl acetate % of less than 18%; and from about 0.5% to about 15% by weight of one or more fragrance compositions. The skin engaging member preferably demonstrates a low level of swelling when contacted or submerged in water.

Another aspect of the invention provides for a hair removal device comprising at least one blade, and a skin engaging member comprising: a water-soluble polymer; ethylene vinyl acetate and a fragrance composition, wherein said skin engaging member swells less than 0.5 mm in accordance with the Swell Test Method defined herein.

Yet another aspect of the invention provides for a hair removal device comprising at least one blade, and a skin engaging member comprising: a water-soluble polymer; ethylene vinyl acetate and a fragrance composition, wherein said skin engaging member has a swell rate of change in mm/min that is from 0 to 0.01 mm/minute in accordance with the Swell Test Method defined herein.

DETAILED DESCRIPTION OF THE INVENTION

I. Skin Engaging Member

Figure 1:
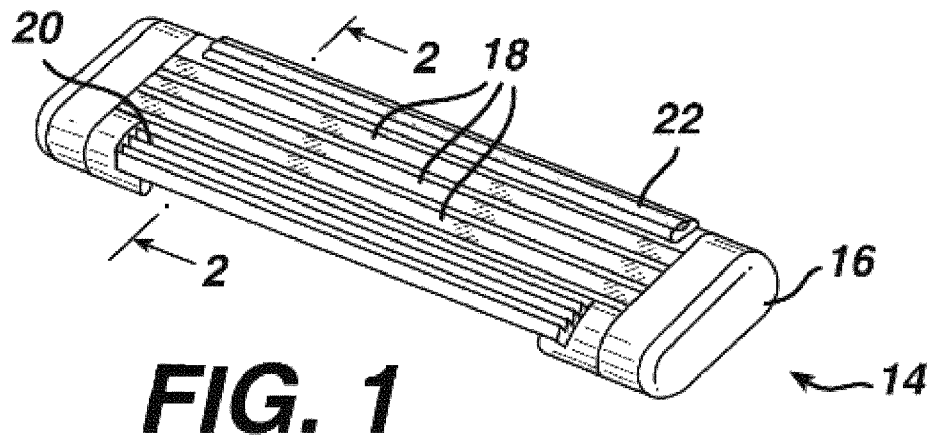
FIG. 1 is a perspective view of a razor cartridge which includes a skin engaging member of the present invention.

The skin engaging member of the present invention is suitable for use on a hair removal device (such as a razor), said skin engaging member consists of one or more layers of a skin engaging member material, which can be of a polymeric material. Multi-layered skin engaging member systems such as those described in U.S. Pat. No. 5,956,848. The skin engaging member can also be made of multiple adjacent strips such as disclosed in U.S. Pat. No. 6,298,559. The skin engaging member comprises at least one skin engaging member. The skin engaging members of the present invention are formed of a polymeric matrix comprising a water soluble polymer and a water-insoluble polymer comprising ethylene vinyl acetate (EVA) and fragrance.

The water-insoluble polymer material can be at a level of from about 22% to about 40%, preferably about 26% to about 40%, of EVA by weight of the skin engaging member. The amount of EVA can also be selected at a level of from about 25% to about 32%, or from about 26% to about 30%. Though higher levels of EVA have been disclosed, having too much EVA (in effect too much water-insoluble polymer) can impact the amount of lubrication and other potential benefits provided by the skin engaging member because it can reduce the amount of other ingredients and water-soluble polymer that can be provided. The EVA can be added as a raw material feed on its own, or can be introduced with other ingredients. For purposes of this invention, the level of EVA refers to total amount of EVA in the skin engaging member regardless of how it is introduced. EVA can be introduced pre-mixed/combined with other ingredients (actives or fillers), or can be combined during mixing steps.

In one embodiment, the EVA is selected to have a % vinyl acetate (% VA) of about 18% or less, possibly less than about 18%, including less than about 12%. In one embodiment the % vinyl acetate can be, as low as about 2% to about 5%, preferably from about 2.5% to 4%. The % vinyl acetate can also be selected at a level of from about 8% to about 15%, or from about 10% to about 13%. "About" as used herein with regards to EVA level and % vinyl acetate can mean±0.1%. Without intending to be bound by theory, it is believed that selecting a grade of EVA with a % vinyl acetate as specified herein provides a matrix material that provides enough structural integrity without limiting the ability of the skin engaging member to provide lubrication over multiple uses. It is believed that a % vinyl acetate can impact the structural integrity benefits provided by the EVA. It is believed that high total amounts of vinyl acetate (which is a function of level of EVA and the % vinyl acetate) can cause the skin engaging member to swell or deform excessively or too early in its lifespan.

In one embodiment, the skin engaging member comprises a total vinyl acetate level of from about 0.2 up to 7.5%, by weight of the skin engaging member, preferably from about 0.4 to about 5.75%. The total vinyl acetate level can also be from about 0.55 to about 4.3%, or from about 0.75 to about 3%. The total vinyl acetate level would be inclusive of the vinyl acetate present in the skin engaging member from EVA or from other sources based on the weight of the skin engaging member. Those of skill in the art will understand that any carrier or other non-active tray or support would not be considered in determining total vinyl acetate level.

Without intending to be bound by theory, it is believed when formulating with an EVA having VA % 18%, it can be preferred to have more EVA present so that the total VA % is from about 4% to about 7.2%, by weight of the skin engaging member. Further, if using an EVA having a 12% VA, it can be preferred to control the EVA levels to have a total VA % from about 2.6 to about 4.8%. Furthermore, if using an EVA having a 9% VA it can be preferred to have a total VA % from about 2.0 to about 3.6%. If using an EVA with a grade of 2.5% VA it can be preferred to have a total VA % from about 0.5 to about 1%.

Without intending to be bound by theory, it is now believed that as % VA increases, the material can become more elastic, less stiff. Though this was seen as an advantage, such as pointed out in U.S. Pat. No. 5,349,750 at col. 2, first paragraph, stating "Increasing the amount of vinyl acetate in an ethylene vinyl acetate copolymer reduces its crystallinity, increases its flexibility, and reduces its hardness. Despite this teaching, it has now been found that having high levels of vinyl acetate, such as 18% or above can have undesirable benefits from this increased flexibility and reduced hardness. Without intending to be bound by theory, it is now believed that use of vinyl acetate with a % VA of higher than 18%, such as EVA with 25% VA grade can result in greater challenge to mechanically retain in a cartridge. It is believed that this can become even more challenging with higher MW PEO grades, which are known to potentially undergo swelling of the water soluble matrix, but also provides desirable lubrication. By using lower % VA grades as described herein, it is believed that a less elastic skin engaging member can be formulated, which enable managing the greater swelling forces of high MW PEO, and/or permit a lower total level of insoluble matrix material.

% VA can be determined on an "as added" basis based on a total material basis of the feed streams. For determining % VA from product post manufacturing, % VA can be measured with many different measurement technologies that are available for compositional analysis. The total amount of insoluble matrix material can be determined by a gravimetric comparison of a completely leached and dried lubricating member with the starting mass. The % VA in the insoluble matrix can be measured by quantitative FTIR spectroscopy such as described by Williams (J. Chem. Educ., 1994, 71 (8), p A195), or by nuclear magnetic resonance to determine relative spectral peak areas to determine the proportion of vinyl acetate present in the skin engaging member as described by Koopmans et. al. (J. Adhesion, 1983, Vol. 15, pp. 117-124). In one embodiment, the % VA is determined on an "as added" basis. In another embodiment, the % VA is determined post production. Those of ordinary skill in the art will understand that % VA should be the same between an "as added" basis and if analyzed post production with minor potential variations plus or minus up to 0.1%, based on analytical method error, potential volatilization of ingredients and other processing factors.

Without intending to be bound by theory it is believed that skin engaging members in accordance with the present invention provides one or more of the following benefits.

Another potentially useful water-insoluble polymer is polystyrene, preferably a general purpose polystyrene or a high impact polystyrene (HIPS) such as Styrenics 5410 from Ineos (i.e. polystyrene-butadiene), such as BASF 495F KG21.

The strip or any portion should contain a sufficient quantity of water-insoluble polymer to provide adequate mechanical strength, both during production and use. Without intending to be bound by theory, it is believed that EVA provides superior toughness and resiliency to HIPS evidenced by slower matrix wear when subjected to abrasion. It is also believed that EVA also allows for lower extrusion and molding process temperatures than HIPS. In one embodiment, the matrix does not include any other water-insoluble polymers other than EVA. In one embodiment, the matrix is free or essentially free (meaning no amount of said ingredient is intentionally added but could be present at trace levels as processing carryover) of polystyrene. In another embodiment, however, EVA can be blended with HIPS or another water-insoluble polymer of blends thereof.

Without intending to be bound by theory, it is believed that the use of EVA in the present invention allows for a lowered extrusion process temperature, for example skin engaging members comprising EVA could be extruded at 120° C., for some formulations even as low as 100 C, compared to skin engaging members comprising high impact polystyrene would could require temperatures around 180° C. This processing flexibility can enable previously unavailable ingredients to be included as they may be able to survive the lower processing temperatures.

In one embodiment, the skin engaging member comprises a solid polymeric matrix having a melting temperature from about 95° C. to about 205° C., said matrix comprising a water-insoluble polymer material comprising ethylene vinyl acetate and combined with a water-soluble polymer material and other optional adjunct or secondary ingredients.

Additional water-insoluble polymers can also be used, in addition to the EVA. Examples of additional water-insoluble polymers include those known in the art and used in skin engaging members found on razors today. Specific water-insoluble polymers which can be used include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof, such as polypropylene/polystyrene blend or polystyrene/impact polystyrene blend. These matrix polymers can also be free or essentially free of one of more of these additional water-insoluble polymers.

Suitable water soluble polymers which can be used in accordance with the present invention include, but are not limited to, one or more of: a polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, silicone polymers, and mixtures thereof. In one embodiment, said water soluble polymer is selected from the group consisting of polyethylene oxide, polyethylene glycol, and a mixture thereof.

In one embodiment, the skin engaging member comprises any other ingredients commonly found in commercially available skin engaging members, such as those used on razor cartridges by GILLETTE®, SCHICK® or BIC®. Non-limiting examples of such skin engaging members include those disclosed in U.S. Pat. Nos. 6,301,785, 6,442, 839, 6,298,558, 6,302,785, and U.S Patent Pubs 2008/060201, and 2009/0223057. In one embodiment, the skin engaging member further comprises a skin engaging member ingredient selected from the group consisting of polyethylene oxide, polyvinyl pyrrolidone, polyacrylamide, hydroxypropyl cellulose, polyvinyl imidazoline, polyethylene glycol, poly vinyl alcohol, polyhydroxyethylmethacrylate, silicone copolymers, sucrose stearate, vitamin E, soaps, surfactants, panthenol, aloe, plasticizers, such as polyethylene glycol; beard softeners; additional lubricants, such as silicone oil, TEFLON® polytetrafluoroethylene powders (manufactured by DuPont), and waxes; essential oils such as menthol, camphor, eugenol, eucalyptol, safrol and methyl salicylate; tackifiers such as Hercules Regalrez 1094 and 1126; non-volatile cooling agents, inclusion complexes of skin-soothing agents with cyclodextrins; fragrances; anti-pruritic/counterirritant materials; antimicrobial/keratolytic materials such as Resorcinol; anti-inflammatory agents such as Candilla wax and glycyrrhetinic acid; astringents such as zinc sulfate; surfactants such as pluronic and iconol materials; compatibilizers such as styrene-b-EO copolymers; mineral oil, polycaprolactone (PCL), and combinations thereof.

Without intending to be bound by theory, it is believed that many potentially useful ingredients can be adversely impacted by conventional skin engaging member extrusion and molding processing conditions. For example, skin engaging members comprising polystyrene could require high temperatures or high pressures for extrusion. These conditions can result in outright or premature decomposition or decrease in efficacy of these ingredients. In one embodiment, the skin engaging member is made at a controlled temperature such as below 130° C.

The water-soluble polymer will preferably comprise at least 50%, more preferably at least 60%, by weight of the skin engaging member, up to about 78%, or up to about 70% of the matrix. The more preferred water soluble polymers are the polyethylene oxides generally known as POLYOX (available from Dow or ALKOX (available from Meisei Chemical Works, Kyoto, Japan). These polyethylene oxides will preferably have mol. wt. of about 100,000 to 10 million, most preferably about 300,000 to 6 million The water-soluble polymeric matrix of the present invention comprises a mixture of high mol. wt. PEO and low mol. wt. PEO. The relative amounts of high and low mol. wt. PEO can respectively be: from about 63.5% to about 95% by weight of the mixture of high and low weight PEO, of a high mol. wt. PEO, or from about 65% to about 90%, or from about 70% to about 75%; and from about 5% to about 36.5% by weight of the mixture of high and low weight PEO, of a low mol. wt. PEO, or from about 10% to about 35%, or from about 25% to about 30%. In one embodiment, the high and low mol. wt. PEO consists essentially of said amounts of high mol. wt. PEO and low mol. wt. PEO. Other polymers can also be present aside from the high and low mol. wt. PEO mixture.

In one embodiment, the mixture of PEO has a high mol. wt. PEO to low mol. wt. PEO ratio of about 1.75:1 to about 19:1, or from about 1.8:1 to about 10:1. In one embodiment, the ratio is greater than 1.8:1. Without intending to be bound by theory, it is believed that such a ratio, of more high mol. wt. PEO to low mol. wt. PEO, compared what has been disclosed, provides improved benefits to the user during the shave, such as improved lubrication and glide over skin during the shaving stroke. Without intending to be bound by theory, it is believed that this can provide a more comfortable and pleasurable shaving experience by decreasing friction on skin and other related irritations. In addition, it is believed that formulating at lower processing temperatures can reduce the molecular weight degradation of the PEO starting materials, and increase the mol. wt. delivered during shaving. This has the additional benefit of reducing the overall level of PEO needed, in turn enabling higher levels of other materials that can be included without a compromise in shaving comfort. Other ingredients which are temperature sensitive, such as fragrance and other skin conditioners and cosmetic agents, can also benefit from extruding at lower temperatures.

As defined here, a high mol. wt. PEO has an average mol. wt. of about 2 million to 10 million Da, preferably of about 5 million Da. Commercially available sources of high mol. wt. PEO include POLYOX COAGULANT ("COAG"). Also, as defined herein, a low mol. wt. PEO has an average mol. wt. of less than 1 million to about 100,000 Da, preferably of about 300,000 Da. Commercially available sources of low mol. wt. PEO include POLYOX WSR-N-750 ("N750"). Another commercially available type of PEO is Polyox WSR 308.

In one embodiment, the mixture of high and low mol. wt. PEO is at a level of from about 20% to about 100% of the skin engaging member, or from about 35% to about 90%, or from about 50% to about 90%, or 75% to about 80%.

In one embodiment, the matrix comprises more PEO than EVA.

Figure 2:
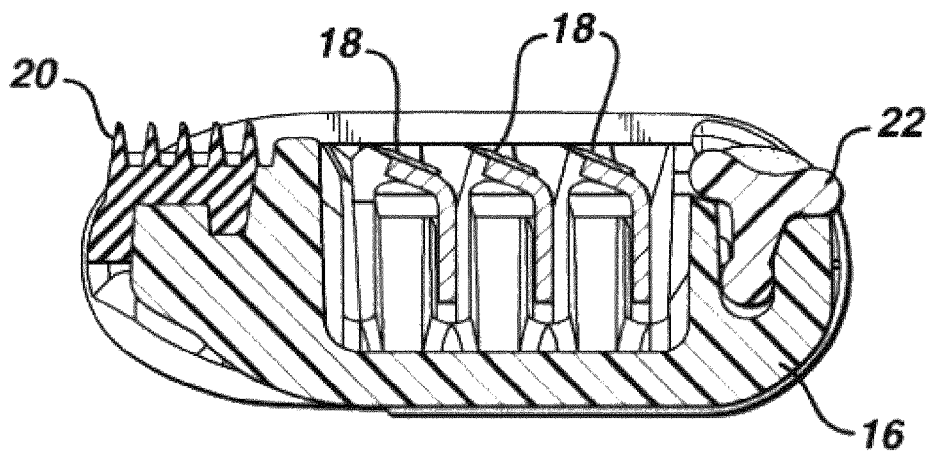
FIG. 2 is a sectional view taken along line 2-2 of FIG. 1.

In one embodiment, the skin engaging member comprises more than one layer, or a base layer and a second layer at least partially coating a portion of said base layer, such as shown in FIG. 2 where skin engaging member 22 has two layers. The mixture of the high and low mol. wt. PEO can be present in either or both layers. Skin engaging members having more than two layers are also within the scope of the present invention.

The skin engaging member of the present invention can be a single uniform composition, or can be formed of more than one layer. In one embodiment, the skin engaging member comprises at least two layers, a top layer and a base layer. In one embodiment, the top layer can have a ratio of water soluble polymers (i.e. PEO) to water insoluble polymers (i.e. EVA) of from about 3:1 to 1:1 by weight. In one embodiment, the base layer can have a ratio of such components of from about 5:4 to about 1:1. In one embodiment, the proportion of water soluble polymers to insoluble polymers in the first layer is higher than a comparable ratio in the second layer.

Furthermore, the skin engaging member can include a sheath and core such as disclosed in U.S. Pat. Nos. 6,298,558 or 7,581,318, wherein the present mixture comprising PEO and EVA can be used as the sheath or core, preferably as the core with the sheath being made of a non-soluble polymer material such as a thermoplastic resin including but not limited to water insoluble polymers like high impact polystyrene, polystyrene, ethylene vinyl acetate, and mixtures thereof, as well as water soluble polymers such as those disclosed herein. In one embodiment, the core can be referred to as the first layer and the sheath as the second layer. In one embodiment, the sheath can comprise the mixture of PEO and EVA of the present invention, or a non-active sheath that does not disperse, dissolve or otherwise release active lubricants during use. In such as case, the sheath would not be considered in determining the weight % of the skin engaging member.

It should be understood that other types of PEO may also be included aside from the high and low mol. wt. PEOs described above (i.e. PEOs of mol. wt. above 10 million, between 1 million and 2 million, and/or below 100,000 Da). Those of skill in the art will understand that if PEOs outside these ranges of high and low mol. wt. PEO are included, the relative ratio of high mol. wt. PEO to low mol. wt. PEO will stay the same but the overall level of each of these PEOs can decrease as other ingredients are added to the skin engaging member. The polyethylene oxide blend may also contain up to about 10% by weight of a lower mol. wt. PEO (i.e. MW<10,000) polyethylene glycol such as PEG-100.

Other optional water soluble or insoluble polymers can also be included in the matrix. In one embodiment, the matrix further comprises from about 0.5% to about 50%, preferably from about 1% to about 20%, polycaprolactone (preferably mol. wt. of 30,000 to 60,000 daltons). See U.S. Pat. No. 6,302,785.

In another embodiment, the skin engaging member may contain other conventional skin engaging member ingredients, such as low mol. wt. water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, antioxidants, preservatives, vitamin E, aloe, cooling agents, essential oils, beard softeners, astringents, medicinal agents, etc. Portions that contain a colorant can be designed to release the colorant (e.g., by leaching or abrasion), and thereby cause the strip to change color during shaving, preferably in response to wear of the colored portion, so as to provide an indication to the user that the skin engaging member and/or the razor cartridge has reached the end of its effective life or the end of its optimum performance A portion may contain, for example, between about 0.1% and about 5.0% (preferably between about 0.5% and 3%) colorant by weight.

II. Fragrance

The fragrances can be added directly into the skin engaging member or can be added in an encapsulated form. In one embodiment, the skin engaging member comprises an effective level of neat fragrance to provide consumer noticeable scent benefits over multiple shaves. In one embodiment, the total level of fragrance can be from about 0.5% to about 15% by weight of one or more fragrance compositions, or from about 2% to about 10%. In one embodiment, a combination of encapsulated fragrance and neat added fragrance are used. In another embodiment, only neat fragrance is used.

In one embodiment, the skin engaging member comprises a high level of fragrance compositions, such as at least about 4%, at least about 5%, at least about 7% or at least 10%, up to 15% by weight of the skin engaging member. Without intending to be bound by theory, it is believed that providing a high level of fragrance can provide an unexpected benefit of improved structural integrity of the skin engaging member during even a single use. It is believed that this can be demonstrated when the skin engaging member is exposed to water for an extended duration such as greater than 5 minutes, up to 10 minutes. In such a situation, it is believed that the skin engaging member of the present invention can experience less swelling compared to skin engaging members comprising fragrance at from about 0.5% to about 4%.

Where the skin engaging member has multiple layers, the fragrance can be present in one or more layers, preferably in the outer most layer so the scent is experienced upon first use, even upon opening the product. In one embodiment, fragrance is added to the layer where ethylene vinyl alcohol is used. In one embodiment, less if any fragrance is used in the base layer(s).

Further, without intending to be bound by theory, it is believed that by using a water insoluble polymer comprising ethylene vinyl acetate the processing and extrusion conditions can be less impactful on the water soluble polymers and any other temperature or pressure sensitive ingredients. With less degradation of the water soluble polymer, it is now believed that less of the water soluble polymer need be added to achieve comparable lubrication benefits compared to skin engaging members using other water insoluble polymers like polystyrene. It is believed that previous formulations of skin engaging members had limited formulation flexibility as the need to deliver high levels of lubrication was a primary objective that required high amounts of water soluble polymer. It is now believed that the use of the specific grades of ethylene vinyl acetate of the present invention provides added formulation flexibility such that other active ingredients such as fragrance can be added to the skin engaging member at sufficiently high a level that they can make a meaningful impact to users.

In one embodiment, the present invention could allow for higher levels of fragrance to be incorporated into the skin engaging member without sacrificing on core lubrication performance Additionally, it is believed that since fragrance compositions are typically volatile, the use of ethylene vinyl acetate as a water insoluble polymer allows for lower temperature extrusion which can allow more of the fragrance to survive processing.

Determination of a suitable fragrance for use in a skin engaging member of the present invention depends on several factors, including whether the scent provided is pleasant to users, and any impacts it can have on processing and storage, as well as the stability and structure of the resulting skin engaging member, particularly if the product is stored for extended amounts of time prior to use, such as several weeks or months. The fragrance raw materials can be neat fragrance oil and/or encapsulated fragrance.

A fragrance for use herein should have an appropriate volatility and balanced blend of top, medium and bottom notes. Very high volatile fragrance may negatively impact process and stability requirements when dealing with extruded skin engaging members. Extremely low volatile fragrance may not be sufficiently noticeable for users. In one embodiment, it is useful to have a fragrance having a flash point of ≥80° C., ≥90° C., such as greater than about 93° C. up to about 95° C. Depending on the type of ethylene vinyl acetate used, different fragrances can be selected.

For example, if selecting a more volatile fragrance, such as one having a flash point between 80-90° C., the processing temperatures would need to be controlled to avoid excessive loss of the fragrance (i.e. extrusion temps below 120° C.). Processing temperatures of the skin engaging member is dependent on a variety of factors, including the type of water insoluble polymer selected. If selecting a less volatile fragrance, such as one having flash point above 90° C., the extrusion temperature can be higher such as above about 120° C., up to about 140° C.

In one embodiment, the fragrance component comprises a plurality of ingredients, such as Ethylene Brassylate, Methyl Dihydro jasmonate, Iso Gamma Super, Pyranol, Nonalactone, Galaxolide, Benzaldehyde, MAYOL, VERDOX, Heliotropin, Coumarin, Floralozone, EBANOL, Ethyl Vanillin, Gamma Decalactone, Ionone Gamma Methyl, Plicatone, Dimethyl Benzyl Carbinyl Butyrate, POLYSANTOL, Precyclemone B, Laevo Trisandol, Undecalactone, Cis-3-hexenyl Salicylate, Iso Butavan, Hexyl Salicylate, NEBULONE, HABANOLIDE, and Ambrettolide. One example of a fragrance in accordance with the present invention is described in detail herein as Fragrance RM. Fragrance RM has coconut scents which can provide a desirable response from users when introduced in a shaving context.

Without intending to be bound by theory, it is believed that the excessive and/or uncontrolled swell of lubrastrip may result in possible loss of shaving closeness, inconsistent delivery of lubricant and less predictable shaving performance. The swell measurement can be carried out upon two different situations, (1) lubrastrip in razor cartridge and (2) lubrastrip out of razor cartridge.

For situation (1), lubrastrip cap height within a cartridge housing can be accurately determined by using (a) Pinnacle dimension measurement equipment (e.g., View Pinnacle 250) or (b) OGP SmartScope multisensor measurement systems (e.g., OGP Smartscope DRS-500) or (c) any high quality optical microscope/digital camera. In (a) & (b) cases, they are high throughput methods. The wetted or water soaked razor cartridges is mounted in fixtures and put onto the measurement device ensuring that cartridge is laid flat in the same orientation.

The laser will detect the cap height relative to other reference positions. To avoid excessive surface water impacting the measurements, a smooth and soft water absorbing paper/cloth is applied to the shaving surface of the razor cartridge to remove any surface water from the skin contacting surface of the skin engaging member.

Swell Test Method

The Swell Test Method as referred to herein can provide a measurement of skin engaging member swell as well as the slope of swelling. The method can be used for situation (c) as follows: 5 lubrastrips are held in a fixture within a clear container which orients the samples parallel to each other, but with none of samples contacting anything at the skin contacting region of the strip. They are further oriented so that the shaving aid dimension normal to the skin contacting plane can be measured with a high resolution digital camera attached to a microscope of about 2× to 3× magnification with distance calibration.

The fixture and clear container are sized so that 150 ml of DI water at a temperature of 68F to 72F will completely submerge the skin engaging member samples. The dimensions of the dry and wet skin engaging member are measured from images taken with a high resolution digital camera attached to a microscope of 3× magnification with a calibrated scale in the image for reference, or a calibrated relationship between image pixel dimension and actual measurement. One example is a Nikon SMZ745T microscope with a Sentech STC-TC202USB-AS camera. The images can be collected, and calibrated distances measured with iSolution Lite software. A focused image is first captured for each of the 5 samples, and the initial dry dimension of the skin engaging member normal to the skin contacting plane is measured to the nearest 0.01 mm from the images, and recorded as the initial dimension prior to water contact, or time=0.

150 ml of DI water at a temperature of 68F to 72F is then added to the container with the fixture and samples to completely submerge all 5 samples, and the time is recorded. Focused images that capture the extent of maximum dimensional change of the skin engaging member normal to the skin contacting plane are taken of all the samples at a time of 5 minutes, then every 5 minutes thereafter up to 30 minutes. The dimension of the skin engaging member normal to the skin contacting plane is measured to the nearest 0.01 mm from each of the images, and recorded as the wet dimension at each corresponding total immersion time.

The results can be calculated as a difference in wet-dry absolute difference, and the difference divided by the initial dimension to get a percent change. The average of 5 measurements is taken as representative of the sample. The swell rate of change (in mm/minute) can be therefore expressed as the slope of the linear best fit of the dimensional change in mm, vs time in minutes at the 5, 10, 15, 20, 25 and 30 minute immersion times.

In one embodiment, the invention provides for a hair removal device comprising at least one blade, and a skin engaging member comprising: a water-soluble polymer; ethylene vinyl acetate and a fragrance composition, wherein said skin engaging member swells less than 0.5 mm, preferably less than 0.43 mm, preferably less than 0.26 mm in accordance with the Swell Test Method defined herein. The swell rate can also be as low as 0.025, as low as 0.22, as low as 0.10 and as low as 0.0.6.

In another embodiment, the invention provides for a hair removal device comprising at least one blade, and a skin engaging member comprising: a water-soluble polymer; ethylene vinyl acetate and a fragrance composition, wherein said skin engaging member has a swell rate of change in mm/min that is from 0 to 0.01 mm/minute in accordance with the Swell Test Method defined herein. The slope can be as low as 0.017, as low as 0.008, as low as 0.007, or even lower.

Figure 4:
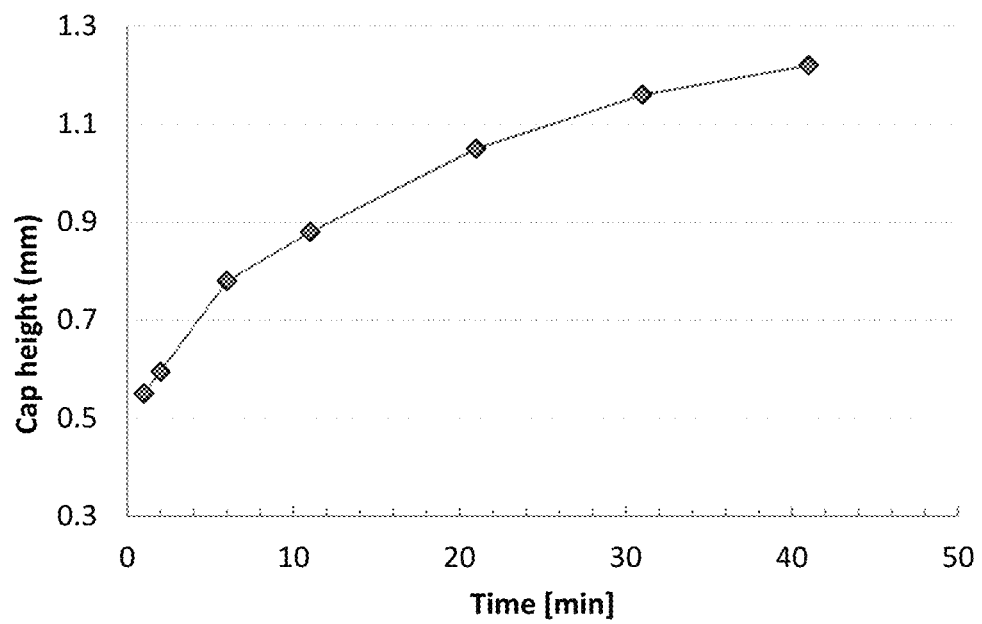
FIG. 4 is a graphical representation of swell performance of an in-market sample, over time.

For example, the swell of a skin engaging member found in the market (sold as HyperGlide by King of Shaves) has been determined and charted over time (see FIG. 4). This sample is analyzed by immersing the entire cartridge squared clear glass container in about 200 ml of DI water such that the entire product is submerged. The sample is place with blades facing up so the skin engaging member can be visualized from the side for imaging analysis. After 30 min immersion, the shave aid has swelled about 0.60 mm Without intending to be bound by theory, it is believed that such an extensive amount of swelling can create loss of shave closeness, particularly for shower users. Also, the non-linear swell behavior makes shave performance less predictable.

For situation (2), one method to measure skin engaging member swelling will be via high quality microscope. First, the produced (or separated from disassembly of cartridge) lubrastrip is mounted in a metal/plastic fixture. Then, the entire sample with fixture is immersed in about 150 ml DI water and the cross-section of the lubrastrip is adjusted horizontally; After the sample has been soaked for certain time intervals (0, 5, 10, 15, 20, 25 & 30 min), immediately use a calibrated microscope to measure the overall height and width and take pictures at each time interval. The swell is constantly monitored till 30 min soaking is completed. Repeat measurements of five lubrastrips are used to determine the average swell.

This method is particularly useful for comparison of a series of lubrastrips samples with different formulations. A series of scented lubrastrip samples can be formulated and tested with this method with net change delta in height shown below in Table B (with different fragrances) and Table D (with one fragrance RM sample at varying levels).

Without intending to be bound by theory, it is now believed that when a hydrophobic liquid oil phase (such as a fragrance composition as described herein) is formulated into an extruded skin engaging member (aka a razor lubrastrip), the skin engaging member can experience product swelling when contacted with water and/or immersed in water. Since skin engaging members comprising ethylene vinyl acetate as a water insoluble polymer for structuring, the resulting extruded skin engaging member can have low wearing rate for wet shaving due to the ethylene vinyl acetate being less likely to wear down over time from friction. This can be an important benefit as it can help maintain the structure of the skin contacting surface of the product. As such, when the product swells, performance benefits can be lost. Controlling the swelling of the skin engaging member is thus an important aspect to maintain so users can experience a more idea shaving geometry as their skin is contacted with the product over multiple uses.

The swelling data described in the Examples shows that a skin engaging member comprising 10% of a fragrance sample RM as described herein. This formulation is tested against similar skin engaging members having the same formulations but for the change in fragrance. The sample with fragrance RM resulted in the least swelling, less swelling even than a similarly formulated skin engaging member without fragrance. See Table B in the Examples section below.

Table D reveals that when holding the formulation constant but decreasing the Fragrance RM ingredient in favor of increased levels of water soluble polymer, the swelling initially increases with higher levels of the fragrance, but levels off at 10%. Surprisingly this is not a linear swell behavior. It is now believed that skin engaging members having at about 10% or more of a fragrance RM offer the best control of swelling.

III. Skin Care Actives

Various skin care actives ("actives") which are commonly used for topical application can also be used in the skin engaging member as a neat product and/or in an encapsulate, or as a coating. Various actives suitable for cosmetic and dermatological use can be used herein. Non-limiting examples of suitable actives include one or more of: Bisabolol and ginger extract, a surfactant derived from olive oil such as OLIVEM 450® and OLIVEM 460®, Lauryl p-Cresol Ketoxime, 4-(1-Phenylethyl)1,3-benzenediol, Lupin (*Lupinus albus*) oil & wheat (*Triticum vulgare*) germ oil unsaponifiables, Hydrolyzed lupin protein, Extract of L-lysine and L-arginine peptides, Oil soluble vitamin C, Evodia rutaecarpa fruit extract, Zinc pidolate and zinc PCA, Alpha-linoleic acid, p-thymol, and combinations thereof; at least one additional skin and/or hair care active selected from the group consisting of sugar amines, vitamin $B_3$, retinoids, hydroquinone, peptides, farnesol, phytosterol, dialkanoyl hydroxyproline, hexamidine, salicylic acid, N-acyl amino acid compounds, sunscreen actives, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), menthyl anthranilate, cetyl pyridinium chloride, tetrahydrocurmin, vanillin or its derivatives, ergothioneine, melanostatine, sterol esters, idebenone, dehydroacetic acid, Licohalcone A, creatine, creatinine, feverfew extract, yeast extract (e.g., PITERA®), beta glucans, alpha glucans, diethylhexyl syringylidene malonate, erythritol, p-cymen-7-ol, benzyl phenylacetate, 4-(4-methoxyphenyl)butan-2-one, ethoxyquin, tannic acid, gallic acid, octadecenedioic acid, p-cymen-5-ol, methyl sulfonyl methane, an avenanthramide compound, fatty acids (especially poly-unsaturated fatty acids), anti-fungal agents, thiol compounds (e.g., N-acetyl cysteine, glutathione, thioglycolate), other vitamins (vitamin B 12), beta-carotene, ubiquinone, amino acids, their salts, their derivatives, their precursors, and/or combinations thereof; and a dermatologically acceparrier. These and other potentially suitable actives are described in greater detail in U.S. Patent Publication No. 2008/0069784.

Additional actives that can be used include those commercially available under the following tradenames: Signaline S, Jojoba Oil, Ceramidone, Net DG, Pal-GHK (Paltenex), Rhodysterol, Vital ET, and combinations thereof.

In another embodiment, the active can be a methyl naphthalenyl ketone. The methyl naphthalenyl ketone can be a 1-(1,2,3,4,5,6,7,8-octahydro-2,3,8,8-tetramethyl-2naphthalenyl)-ethan-1-one molecule or an isomer or derivative thereof. Commercially available as Iso-E-Super from IFF of New York. Other sensates can also be used, including those which have ability to up-regulate the TRPM8 receptor, which has been described as the cool menthol receptor. Non-limiting examples of suitable TRPM8 regulators include: p-methane-3,8-diol; Isopulegol; Menthoxypropane-1,2,-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, and mixtures thereof.

The active ingredient can also be one or more skin care actives suitable for topical use. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. The 11$^{th}$ edition of PCPC's International Cosmetic Ingredient Dictionary and Handbook, along with the 2005 PCPC International Buyer's Guide both provide useful compositions which may be suitable for incorporation into the skin engaging member of the present invention. Examples of these ingredient classes include: abrasives, absorbents, aesthetic components such as pigments, colorings/colorants, essential oils, skin sensates, astringents, etc. (e.g., clove oil, camphor, eucalyptus oil, eugenol, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, fatty alcohols and fatty acids, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin-conditioning agents, skin soothing and/or healing agents and derivatives, skin treating agents, thickeners, and vitamins and derivatives thereof.

Additional non-limiting examples of additional suitable skin treatment actives are included in U.S. 2003/0082219 in Section I (i.e. hexamidine, zinc oxide, and niacinamide); U.S. Pat. No. 5,665,339 at Section D (i.e. coolants, skin conditioning agents, sunscreens and pigments, and medicaments); and US 2005/0019356 (i.e. desquamation actives, anti-acne actives, chelators, flavonoids, and antimicrobial and antifungal actives). It should be noted, however, that many materials may provide more than one benefit, or operate via more than one mode of action. Therefore, classifications herein are made for the sake of convenience and are not intended to limit the active to that particular application or applications listed.

a. Cooling Agents

Non-limiting examples of suiooling agents include: L-menthol; p-methane-3,8-diol; Isopulegol; Menthoxypropane-1,2,-diol; Curcumin; Menthyl Lactate (such as Frescolat ML by Symrise); Gingerol; Icilin; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, Menthone Glyerine Acetal; Coolact 10; and mixtures thereof. These and other cooling agents are known and described in various publications, such as U.S. Patent No. 2008/0300314A1, U.S. Pat. Nos. 5,451,404 and 7,482,373. In yet another embodiment, the cooling agent comprises one or more of the cooling agents previously described for use in various shave aids. See e.g., U.S. Pat. Nos. 5,095,619; 5,713,131; 5,095,619; 5,653,971; 6,298,558; 6,944,952; and 6,295,733.

In one embodiment, the skin engaging member further comprises one or more cooling agents. It is now well established that sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. The TRPM8 nomenclature for the receptor comes from its characterization as a non-selective cation channel of the transient receptor potential (TRP) family that is activated by stimuli including low temperatures, menthol and other chemical coolants. However, the precise mechanisms underlying the perception of a pleasant cooling sensation on skin or oral surfaces are presently not clearly understood. While it has been demonstrated that the TRPM8 receptor is activated by menthol and other coolants, it is not fully understood what other receptors may be involved and to what extent these receptors need to be stimulated or perhaps suppressed in order that the overall perceived sensation would be pleasant, cooling and refreshing.

For example, menthol is widely used as a cooling agent, but menthol can also produce other sensations including tingling, burning, prickling and stinging as well as a minty smell and bitter taste. Thus, it can be inferred that menthol acts on many different receptors, including cold, warm, pain and taste receptors. However, it is not readily discernible how to isolate which receptor activities would result in a specific sensation such as pleasant cooling without the undesirable sensations such as bitterness or irritation. Neither is it apparent how to control the activity of coolants or other sensory agents such that only the desired sensation is elicited from use of a particular sensory agent. As such, the present invention is focused on the addition of specific synthetic derivatives of cyclohexane (described above) to act as sensates to deliver cooling benefit to users during the hair removal process. Additional sensates can be used to further supplement the cooling feel.

A large number of coolant compounds of natural or synthetic origin are known. The most well-known compound is menthol, particularly l-menthol, which is found naturally in peppermint oil, notably of Mentha arvensis L and Mentha viridis L. Of the isomers of menthol, the l-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The biggest difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and l-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-

201]. This study demonstrated the outstanding sensory properties of l-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as FRESCOLAT® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150, 052; 4,153,679; 4,157,384; 4,178,459 and 4,230,688.

Additional ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136, 163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyealanine ethyl ester. Menthyl esters including those of amino acids such as glycine and alanine are disclosed e.g., in EP 310,299 and in U.S. Pat. Nos. 3,111,127; 3,917,613; 3,991, 178; 5,5703,123; 5,725,865; 5,843,466; 6,365,215; 6,451, 844; and 6,884,903. Ketal derivatives are described, e.g., in U.S. Pat. Nos. 5,266,592; 5,977,166 and 5,451,404.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., *J. Pharm. Pharmacol.* (1983), 35:110-112. Reviews on the coolant activity of menthol and synthetic coolants include H. R. Watson, et al. *J. Soc. Cosmet. Chem.* (1978), 29, 185-200 and R. Eccles, *J. Pharm. Pharmacol.*, (1994), 46, 618-630.

IV. Encapsulated Actives

In one embodiment, the skin engaging member of the present invention further comprises at least one encapsulated active. The encapsulated active can be a thermally resilient skin care active or another skin care composition, such as a cooling agent. In one embodiment, the level of said at least one encapsulated active (including the weight of the capsule and encapsulated active) is from about 0.01% to about 50% by weight of said skin engaging member, alternatively from about 10% to about 45%, alternatively from about 15% to about 35%. The encapsulated actives can contain the same ingredients or different ingredients. The encapsulated actives can also include mixtures of ingredients.

The encapsulated can be a cyclodextrin inclusion complex such as described in U.S. Pat. No. 5,653,971, and, U.S. Pat. No. 5,713,131 and/or another encapsulation technology. The thermally resilient skin care agents of the present invention can be included as a neat ingredient (as a direct addition into the composition) and/or in an encapsulate. In one embodiment, one or more of the thermally resilient skin care actives can be present in both a neat form and in an encapsulate. In one embodiment, one of the thermally resilient skin care actives can be in a neat form and thermally resilient skin care active can be in a capsule.

In one embodiment, encapsulated active comprises more than one cooling agent, for example L-menthol+Methyl lactate (Frescolat ML); L-menthol+Menthone Glycerine Acetal (Frescolat MGA); or L-menthol+Coolact 10. In yet another embodiment, the encapsulated active comprises at least one cooling agent and a fragrance, a mineral oil, or a combination thereof. In another embodiment, the cooling agent comprises a mixture of menthol and menthyl lactate, such as described in WO 2007115593 (commercially available as Fresocolat Plus), or the eutectic mixture of menthol and menthyl lactate in a ratio of weight in the range of 1:4 to 4:1, as described in U.S. Pat. No. 6,897,195.

Suitable cooling agents which can be utilized include non-volatile menthol analogs such as menthyl lactate, menthyl ethoxyacetate, menthone glycerinacetal, 3-1menthoxypropane-1,2-diol, ethyl 1-menthyl carbonate, (IS, 3S,4R)-p-menth-8-en-3-ol, menthyl pyrrolidone 25 carboxylate, N-substituted-p-menthane-3-carboxamides (as described in U.S. Pat. No. 4,136,163, which is incorporated herein by reference) including, for example, N-ethyl-pmenthane-3-carboxamide, acyclic carboxamides Suitable skin-soothing agents which can be utilized in the cyclodextrin inclusion complex include menthol, camphor, eugenol, eucalyptol, safrol, methyl salicylate, and the afore described menthol analogs. Any suitable cyclodextrin may be utilized to form the inclusion complex including alphacyclodextrin, beta-cyclodextrin, gamma-cyclodextrin and modified cyclodextrins such as hydroxypropyl-beta-cyclodextrin, methyl-beta-cyclodextrin, and acetyl-betacyclodextrin. The preferred cyclodextrins are betacyclodextrin and gamma-cyclodextrin.

When the matrix material comprises a cyclodextrin inclusion complex, the matrix material may also advantageously comprise up to about 10%, preferably about 2 to 7%, by weight of a displacing agent which displaces the skin-soothing agent from the inclusion complex upon contact with water, thereby enhancing the release of the skin-soothing agent from the skin engaging member material during use. The displacing agent is a material which is capable of forming a more stable complex with the cyclodextrin than the complex formed with the skin soothing agent and, thus, displaces the skin-soothing agent from the complex when the skin engaging member is contacted with water. Suitable displacing agents include surfactants, benzoic acids, and certain amines (e.g. urea). Further details with respect to the aforementioned cooling agents, cyclodextrin inclusion complexes and displacing agents may be found in U.S. Pat. No. 5,653,971, and, U.S. Pat. No. 5,713,131.

Nonlimiting examples of encapsulation technology other than cyclodextrin complexes include the nano and micro particles described in U.S. Pat. No. 7,115,282. The nanoparticles of the present invention are hydrophobic in nature. In one embodiment, the nano-particles have an average diameter in the range from about 0.01 micron to about 10 microns, or from about 0.05 microns to about 5 microns, or from about 0.1 microns to about 2 microns. This linear dimension for any individual particle represents the length of the longest straight line joining two points on the surface of the particle. In one embodiment, a portion of the nano-particles are encapsulated into one or more water-sensitive micro-particles. In one embodiment, the majority of the nano-particles present in the skin engaging member are encapsulated into said water-sensitive micro-particles. The micro-particles have an average particle size of from about 2.0 microns to about 100 microns, or from 20 microns to about 100 microns.

In one embodiment the level of active or actives in the encapsulated active ranges from about 20 to about 90%, preferably from about 30% to about 75% by weight of the nano-particles. In one embodiment the level of the active or actives in the encapsulated active ranges from about 10% to about 60%, or from about 30% to about 50% by weight of the micro-particles. Lower levels of the encapsulated active can also be used, such as low as 10%, or as low as 5%, or as low as 1%.

V. Hair Removal Head

The hair removal device generally comprises a hair removal head and a handle or grip portion, upon which the hair removal head is mounted. The hair removal device can be a manual or power driven and can be used for wet and/or dry application. The hair removal head can include a wide scraping surface such as where the hair removal device is used with a depilatory, or a razor cartridge where the device is a shaving razor. The hair removal head may be replaceable or pivotally connected to a cartridge connecting structure. In an aspect, the cartridge connecting structure includes at least one arm to releasably engage the hair removal head.

The hair removal head comprises one or more elongated edges positioned between said first and said second end, said one or more elongated edges comprising a tip extending towards said first end. Where the hair removal head is a razor cartridge the one or more elongated edges can include blades. For example, U.S. Pat. No. 7,168,173 generally describes a FUSION® razor that is commercially available from THE GILLETTE COMPANY® which includes a razor cartridge with multiple blades. Additionally, the razor cartridge may include a guard as well as a skin engaging member. A variety of razor cartridges can be used in accordance with the present invention. Non-limiting examples of suitable razor cartridges, with and without fins, guards, and/or shave aids, include those marketed by THE GILLETTE COMPANY® under the FUSION®, VENUS® product lines as well as those disclosed in U.S. Pat. Nos. 7,197,825, 6,449,849, 6,442,839, 6,301,785, 6,298,558; 6,161,288, and U.S. Patent Publ. 2008/060201. Those of skill in the art will understand that the present skin engaging member can be used with any currently marketed system or disposable razor, including those having 1, 2, 3, 4 or 5 blades. Another example of a hair removal device is a scraping edge for use with a hair removal composition, i.e. a depilatory.

In one embodiment, said at least one skin engaging member is located on the portion of the cartridge that contacts skin during the hair removal process, forward and/or aft of the blades. A feature "forward" of the one or more elongated edges, for example, is positioned so that the surface to be treated with by the hair removal device encounters the feature before it encounters the elongated edges. A feature "aft" of the elongated edge is positioned so that the surface to be treated by the hair removal device encounters the feature after it encounters the elongated edges. Where more than one skin engaging members is provided on the hair removal device, they can be the same or different. By different, meaning having a different carrier, a different skin engaging member, or wherein both sheath and composition are different. In one embodiment, where multiple skin engaging members are present on the cartridge, at least one of the skin engaging members is a skin engaging member of the present invention, this skin engaging member can be the one forward or aft of the blades. In another embodiment, both skin engaging members are within the scope of the present invention.

In one embodiment, the cartridge comprises a guard comprising at least one elongated flexible protrusions to engage a user's skin. In one embodiment, at least one flexible protrusions comprises flexible fins generally parallel to said one or more elongated edges. In another embodiment, said at least one flexible protrusions comprises flexible fins comprises at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/flexible fin bars); 2008/0034590 (disclosing curved guard fins); 2009/0049695A1 (disclosing an elastomeric guard having guard forming at least one passage extending between an upper surface and a lower surface). In one embodiment, said skin engaging member is positioned on the cartridge aft of the guard and forward of said elongated edge. In another embodiment, the skin engaging member is positioned on the cartridge forward of the guard. This embodiment can be particularly useful to deliver the skin engaging member prior to contact with the guard.

VI. Method of Making

Skin engaging member of the present invention is made by extrusion or another high temperature processing, such as injection molding, compression molding, compacting, ultrasonic or radio frequency sintering, and slot coating. High temperature processing degrades/decomposes the water soluble polymers (PEO) as well as the additional benefit ingredients. In one embodiment with EVA grade Elvax 660 (purchased from Dupont) in the skin engaging member, the extrusion process temperature is lowered to 110° C. In one embodiment, the skin engaging member comprising the thermally resilient skin care active can further be coated or layered with another skin engaging member. In one embodiment, all of the components of the strip, including the high mol. wt. PEO and low mol. wt. PEO mixture can be blended alone or in combination with other ingredients prior to molding or extrusion. It can be preferred that the components are free flowing powders, however, liquid skin actives may be adsorbed onto one or more of the other components in the strip that are in powder form.

In one embodiment, the process of forming a skin engaging member comprises the step of: providing a high mol. wt. and a low mol. wt. PEO feed comprising: from about 60% to about 95% by weight of the PEO feed of a high mol. wt. PEO; and from about 5% to about 30% by weight of the PEO feed of a low mol. wt. PEO. EVA is included as an additional polymer, and other ingredients can also be included with the PEO feed or before or after this PEO feed. Those of skill will understand that if additional PEOs (which do not qualify as high or low mol. wt. PEO) are included in this feed, these other PEOs would not be counted as a portion of the high mol. wt. and low mol. wt. PEO feed.

The PEO feed can be combined with a second feed if additional ingredients are desired. The feed or feeds can be mixed and processed through a step of extrusion through a die to form a skin engaging member suitable for use as a skin engaging member. As will be explained below, said step of extruding can include subjecting said mixture to a pressure of from about 1000 psi to about 7500 psi and/or a temperature of from about 100° C. to about 160° C.

Fragrance can be added with the PEO and or the EVA feeds or in a separate feed.

The blended components may be extruded through a Rondol 18, 18 mm diameter extruder with a barrel pressure of about 500-1000 psi, a rotor speed of about 10 to 50 rpm, and a temperature of about 100°–160° C. and a die temperature of about 100°-160° C. Alternatively, a 1½ inch single screw extruder may be employed with a processing temperature of 100°–160° C., preferably 110-130° C., a screw speed of 20 to 50 rpm, preferably 25 to 50 rpm, and an extrusion pressure of 1800 to 7500 psi, preferably 4000 to 6500 psi. Other extrusion conditions can also be employed. The extruded strip is cooled to about 25° C. To injection mold the strips it is preferred to first extrude the powder blend into pellets. This can be done on a 1¼ or 1½ inch single screw extruder at a temperature of 100°-140° C., preferably 110°-130° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 100° to 185° C., preferably from 110° to 145° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds. In one embodiment, one or more feeds can be preheated or they can be fed in at ambient temperature.

In one embodiment, the process further comprises a step of providing a skin engaging member receiving region (such as a portion of a first layer or base or sheath) and distributing a volume of the PEO feed into said skin engaging member receiving region (to form a second layer or core). Where a sheath and core system are used, the sheath can be performed by molding and the core can be thereafter formed within the sheath by providing said PEO mixture in a fluid or flowable form (such as a liquid or powder) then solidifying it such as by pressurizing, heating and or ultrasonically compressing said PEO feed within said skin engaging member receiving region. Non-limiting examples of ways to form such skin engaging members are disclosed in U.S. Pat. Nos. 6,298,558 or 7,581,318 as well as WO 2011/047221.

VII. Details on Figures

Figure 3:
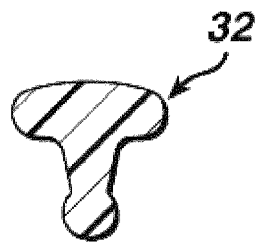
FIG. 3 is a side elevation view of second type of skin engaging member of the present invention.
Figure 5:
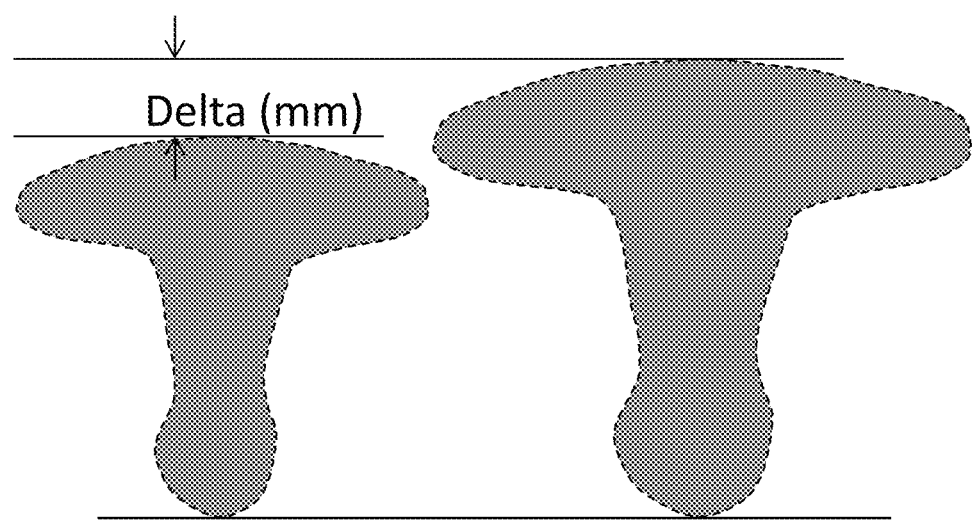
FIG. 5 is a graphical representation of a skin engaging member is a cross section view taken transverse to a longitudinal (major) axis of the skin engaging member where the image shown in dashed lines is pre-soaking and the image in solid lines show a swelled skin engaging member.

Referring to FIGS. 1 and 2, the razor cartridge 14 includes housing 16, which carries three blades 18, a finned elastomeric guard 20, and a skin engaging member 22 located on a skin-engaging portion (in this case the cap) of the cartridge. Skin engaging member 22 is shown having two layers, the first layer can be the matrix and encapsulated active of the present invention, and the second layer can be a conventional shave aid, or vice versa. The skin engaging member is preferably locked in (via adhesive, a fitment, or melt bonding) an opening or on a plate or other flat surface in the rear of the cartridge. Skin engaging member 32, shown in FIG. 3, is similar to skin engaging member 22, except that skin engaging member 32 has a homogeneous composition throughout and a uniform, slightly curved to flat upper surface. FIG. 4 is a graphical representation of swell performance over time of a sample with a skin engaging member commercially available from King of Shaves Hyperglide razor. FIG. 5 is a graphical representation of a skin engaging member is a cross section view taken transverse to a longitudinal (major) axis of the skin engaging member where the image shown in dashed lines is pre-soaking and the image in solid lines show a swelled skin engaging member. Swelling measurements are taken of the surface of the skin engaging member at the skin contacting surface before wetting, and over various time points when contacted with water.

VIII. Examples

TABLE A

Samples of scented and unscented skin engaging members can be formulated as follows (by wt %).

| Material | Example A | Example B | Example C |
| --- | --- | --- | --- |
| EVA with 9% VA (Elvax 750) | 27.00 | 27.00 | 0.00 |
| High Impact Polystyrene | 0.00 | 0.00 | 27.00 |
| Carowax 4600 PEG | 5.00 | 5.00 | 5.00 |
| Polycaprolactone | 5.00 | 5.00 | 5.00 |
| Colorant | 4.00 | 4.00 | 4.00 |
| Sample Fragrance | 0.00 | 10.00 | 10.00 |
| Polyox Coag. [Dow] | 35.38 | 29.38 | 29.38 |
| Polyox N750 [Dow] | 23.62 | 19.62 | 19.62 |
| Total | 100 | 100 | 100 |

TABLE B

Swell (in mm) over time results of newly produced lubrastrips (net height change in room temp. DI water bath). Samples following Example B have different fragrance compositions but each at 10%.

| Sample EVA Strip | 5 min (mm) | 10 min (mm) | 15 min (mm) | 20 min (mm) | 25 min (mm) | 30 min (mm) | Slope (mm/min) |
| --- | --- | --- | --- | --- | --- | --- | --- |
| Example A | 0.15 | 0.22 | 0.29 | 0.35 | 0.38 | 0.40 | 0.010 |
| Example B (Fragrance FF) | 0.13 | 0.27 | 0.38 | 0.46 | 0.53 | 0.56 | 0.017 |
| Example B (Fragrance RL) | 0.07 | 0.16 | 0.19 | 0.23 | 0.26 | 0.28 | 0.008 |
| Example B (Fragrance PM) | 0.11 | 0.16 | 0.21 | 0.24 | 0.26 | 0.29 | 0.007 |
| Example B (Fragrance JO) | 0.18 | 0.25 | 0.30 | 0.35 | 0.38 | 0.38 | 0.008 |
| Example B (Fragrance FL) | 0.18 | 0.26 | 0.29 | 0.35 | 0.37 | 0.39 | 0.008 |
| Example B (Fragrance RM) | 0.06 | 0.10 | 0.22 | 0.22 | 0.25 | 0.26 | 0.008 |
| Example C (Fragrance RM) | 0.25 | 0.41 | 0.52 | 0.59 | 0.64 | 0.69 | 0.017 |

TABLE C

Average % weight loss over time of sample strips of the following formulation. 10 strips of each of following samples is placed in an open glass jar with weight measured at 1 day and at 30 days at varying temperatures. Flash point for each fragrance is shown. In one embodiment, the fragrance for use with this invention has a flash point above 93° C.

| Sample strip | Wt % loss 40° C./1 day | Wt % loss 40° C./30 day | Wt % loss 50° C./1 day | Wt % loss 50° C./30 day | Flash point (° C.) |
|---|---|---|---|---|---|
| 0% Fragrance | 0.25 | 0.09 | 0.36 | 0.24 | |
| Example B (Fragrance RL) | 1.36 | 5.33 | 2.25 | 7.14 | 84 |
| Example B (Fragrance JO) | 1.96 | 5.89 | 2.92 | 6.96 | 85 |
| Example B (Fragrance FF) | 1.10 | 6.33 | 1.56 | 6.06 | 87 |
| Example B (Fragrance PM) | 0.90 | 3.74 | 1.39 | 5.68 | 90 |
| Example B (Fragrance RL) | 1.58 | 6.17 | 2.26 | 7.20 | 92 |
| Example B (Fragrance RM) | 0.64 | 4.86 | 0.89 | 5.95 | 93 |

From the data captured in Table C, it is believed that samples with Fragrance RM had the lowest initial weight loss (1 day=0.64%) as well as low weight loss after 30 days at varying temperatures. In addition to the reduced swelling behavior, it is believed that a skin engaging member comprising Fragrance RM can be particularly desirable.

TABLE D

Swell results of a strip in accordance with Example B with varying levels of sample RM fragrance (net height change in water). Changes in fragrance level offset by varying level of Polyox Coag/Polyox N750 (but maintained at same ratio of 1:5:1). Other ingredients maintained at same level (i.e. EVA maintained at 27%). Samples are immersed in room temperature water baths for the amount of time listed below with swelling measurements taken at the skin engaging surface of the strip.

| Wt % RM added: | 5 min (delta, mm) | 10 min (delta, mm) | 15 min (delta, mm) | 20 min (delta, mm) | 25 min (delta, mm) | 30 min (delta, mm) | Slope mm/min |
|---|---|---|---|---|---|---|---|
| 2% RM | 0.13 | 0.19 | 0.24 | 0.28 | 0.30 | 0.32 | 0.008 |
| 3% RM | 0.14 | 0.23 | 0.29 | 0.34 | 0.36 | 0.37 | 0.009 |
| 4% RM | 0.21 | 0.27 | 0.31 | 0.36 | 0.40 | 0.43 | 0.009 |
| 7.5% RM | 0.13 | 0.22 | 0.28 | 0.34 | 0.36 | 0.38 | 0.010 |
| 10% RM | 0.06 | 0.1 | 0.22 | 0.22 | 0.25 | 0.26 | 0.008 |
| 12.5% RM | 0.10 | 0.16 | 0.2 | 0.23 | 0.28 | 0.30 | 0.008 |

Fragrance Sample RM is made having the following formulation:

| Material | % by weight of perfume composition |
|---|---|
| Ethylene Brassylate | 10-20 |
| Methyl Dihydro jasmonate | 10-20 |
| Iso Gamma Super | 5-15 |
| Pyranol | 5-15 |
| Nonalactone | 0.001-10 |
| Galaxolide | 0.001-10 |
| Benzaldehyde | 0.001-5 |
| Mayol | 0.001-5 |
| Verdox | 0.001-5 |
| Heliotropin | 0.001-5 |
| Coumarin | 0.001-5 |
| Floralozone | 0.001-5 |
| Ebanol | 0.001-5 |
| Ethyl Vanillin | 0.001-5 |
| Gamma Decalactone | 0.001-5 |
| Ionone Gamma Methyl | 0.001-5 |
| Plicatone | 0.001-5 |
| Dimethyl Benzyl Carbinyl Butyrate | 0.001-5 |
| Polysantol | 0.001-5 |
| Precyclemone B | 0.001-5 |
| Laevo Trisandol | 0.001-5 |
| Undecalactone | 0.001-5 |
| Cis-3-hexenyl Salicylate | 0.001-5 |
| Iso Butavan | 0.001-5 |
| Hexyl Salicylate | 0.001-5 |
| Nebulone | 0.001-5 |
| Habanolide | 0.001-5 |
| Ambrettolide | 0.001-5 |

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern. Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair removal device comprising at least one blade and a skin engaging member, the skin engaging member comprising:
   a. about 50% to about 78% of a water-soluble polymer by weight of the skin engaging member;
   b. about 22% to about 40% of an ethylene vinyl acetate by weight of the skin engaging member, the ethylene vinyl acetate having a vinyl acetate % of about 18 or less, wherein the ethylene vinyl acetate is selected from the group consisting of:
      i. an ethylene vinyl acetate having 18% vinyl acetate, and the skin engaging member has a total vinyl acetate level of from about 4% to about 7.2%, by weight of the skin engaging member;
      ii. an ethylene vinyl acetate having 12% vinyl acetate, and the skin engaging member has a total vinyl acetate level of from about 2.6% to about 4.8%, by weight of the skin engaging member;
      iii. an ethylene vinyl acetate having 9% vinyl acetate, and the skin engaging member has a total vinyl acetate level of from about 2.0% to about 3.6%, by weight of the skin engaging member;
      iv. an ethylene vinyl acetate having 2.5% vinyl acetate, and the skin engaging member has a total vinyl acetate level of from about 0.5% to about 1%, by weight of the skin engaging member; and
      v. a mixture thereof; and
   c. about 0.5% to about 15% of a fragrance composition by weight of the skin engaging member, the fragrance composition comprising Fragrance RM, wherein the Fragrance RM consists of Ethylene Brassylate, Methyl Dihydro jasmonate, Iso Gamma Super, Pyranol, Nonalactone, Galaxolide, Benzaldehyde, MAYOL, VERDOX, Heliotropin, Coumarin, Floralozone, EBANOL, Ethyl Vanillin, Gamma Decalactone, Ionone Gamma Methyl, Plicatone, Dimethyl Benzyl Carbinyl Butyrate, POLYSANTOL, Precyclemone B, Laevo Trisandol, Undecalactone, Cis-3-hexenyl Salicylate, Iso Butavan, Hexyl Salicylate, NEBULONE, HABANOLIDE, and Ambrettolide.

2. The hair removal device of claim 1, wherein the fragrance composition comprises at least about 4% by weight of the skin engaging member.

3. The hair removal device of claim 1, further comprising a second water-insoluble polymer.

4. The hair removal device of claim 3, wherein the second water-insoluble polymer comprises at least one of polyethylene, polypropylene, polystyrene, butadiene-styrene copolymer, polyacetal, acrylonitrile-butadiene-styrene copolymer, ethylene vinyl acetate copolymer, polyurethane, or blends thereof.

5. The hair removal device of claim 1, wherein the water-soluble polymer comprises polyethylene oxide.

6. The hair removal device of claim 1, wherein the fragrance composition has a flash point of greater than or equal to 90° C.

7. A hair removal device comprising at least one blade and a skin engaging member, the skin engaging member comprising:
   a. about 50% to about 78% of a water-soluble polymer by weight of the skin engaging member;
   b. about 22% to about 40% of an ethylene vinyl acetate by weight of the skin engaging member, the ethylene vinyl acetate having a vinyl acetate % of about 18 or less, wherein the ethylene vinyl acetate is selected from the group consisting of:
      i. an ethylene vinyl acetate having 18% vinyl acetate, and the skin engaging member has a total vinyl acetate level of from about 4% to about 7.2%, by weight of the skin engaging member;
      ii. an ethylene vinyl acetate having 12% vinyl acetate, and the skin engaging member has a total vinyl acetate level of from about 2.6% to about 4.8%, by weight of the skin engaging member;
      iii. an ethylene vinyl acetate having 9% vinyl acetate, and the skin engaging member has a total vinyl acetate level of from about 2.0% to about 3.6%, by weight of the skin engaging member;
      iv. an ethylene vinyl acetate having 2.5% vinyl acetate, and the skin engaging member has a total vinyl acetate level of from about 0.5% to about 1%, by weight of the skin engaging member; and
      v. a mixture thereof; and
   c. about 0.5% to about 15% of a fragrance composition by weight of the skin engaging member,
   wherein the fragrance composition is not encapsulated and wherein the skin engaging member swells less than 0.50 mm in accordance with the Swell Test Method defined herein, wherein the fragrance composition comprises Fragrance RM, the Fragrance RM consisting of Ethylene Brassylate, Methyl Dihydro jasmonate, Iso Gamma Super, Pyranol, Nonalactone, Galaxolide, Benzaldehyde, MAYOL, VERDOX, Heliotropin, Coumarin, Floralozone, EBANOL, Ethyl Vanillin, Gamma Decalactone, Ionone Gamma Methyl, Plicatone, Dimethyl Benzyl Carbinyl Butyrate, POLYSANTOL, Precyclemone B, Laevo Trisandol, Undecalactone, Cis-3-hexenyl Salicylate, Iso Butavan, Hexyl Salicylate, NEBULONE, HABANOLIDE, and Ambrettolide.

8. The hair removal device of claim 7, wherein the skin engaging member swells less than 0.26 mm in accordance with the Swell Test Method defined herein.

9. A hair removal device comprising at least one blade and a skin engaging member, the skin engaging member comprising:
   a. about 50% to about 78% of a water-soluble polymer by weight of the skin engaging member;
   b. about 22% to about 40% of an ethylene vinyl acetate by weight of the skin engaging member, the ethylene vinyl acetate having a vinyl acetate % of about 18 or less, wherein the ethylene vinyl acetate is selected from the group consisting of:
      i. an ethylene vinyl acetate having 18% vinyl acetate, and the skin engaging member has a total vinyl acetate level of from about 4% to about 7.2%, by weight of the skin engaging member;
      ii. an ethylene vinyl acetate having 12% vinyl acetate, and the skin engaging member has a total vinyl acetate level of from about 2.6% to about 4.8%, by weight of the skin engaging member;
      iii. an ethylene vinyl acetate having 9% vinyl acetate, and the skin engaging member has a total vinyl acetate level of from about 2.0% to about 3.6%, by weight of the skin engaging member;
      iv. an ethylene vinyl acetate having 2.5% vinyl acetate, and the skin engaging member has a total vinyl acetate level of from about 0.5% to about 1%, by weight of the skin engaging member; and
      v. a mixture thereof; and
   c. about 0.5% to about 15% of a fragrance composition by weight of the skin engaging member,
wherein the fragrance composition is not encapsulated and wherein the skin engaging member has a swell rate of change in mm/min that is less than or equal to 0.01 and greater than or equal to zero in accordance with the Swell Test Method defined herein,
wherein the fragrance composition comprises Fragrance RM, the Fragrance RM consisting of Ethylene Brassylate, Methyl Dihydro jasmonate, Iso Gamma Super, Pyranol, Nonalactone, Galaxolide, Benzaldehyde, MAYOL, VERDOX, Heliotropin, Coumarin, Floralozone, EBANOL, Ethyl Vanillin, Gamma Decalactone, Ionone Gamma Methyl, Plicatone, Dimethyl Benzyl Carbinyl Butyrate, POLYSANTOL, Precyclemone B, Laevo Trisandol, Undecalactone, Cis-3-hexenyl Salicylate, Iso Butavan, Hexyl Salicylate, NEBULONE, HABANOLIDE, and Ambrettolide.

10. The hair removal device of claim 9, wherein the skin engaging member demonstrates a slope of 0.007 to 0.008 in accordance with the Swell Test Method defined herein.

* * * * *